(12) United States Patent
Okazaki et al.

(10) Patent No.: US 7,394,081 B2
(45) Date of Patent: Jul. 1, 2008

(54) RADIOISOTOPE PRODUCTION APPARATUS AND RADIOPHARMACEUTICAL PRODUCTION APPARATUS

(75) Inventors: Takashi Okazaki, Hitachinaka (JP); Kazuki Tsuchida, Mito (JP); Hirofumi Seki, Hitachi (JP); Robert W. Hamm, Pleasanton, CA (US)

(73) Assignee: Hitachi, Ltd., Tokyo (JP)

( * ) Notice: Subject to any disclaimer, the term of this patent is extended or adjusted under 35 U.S.C. 154(b) by 450 days.

(21) Appl. No.: 11/088,208

(22) Filed: Mar. 24, 2005

(65) Prior Publication Data

US 2005/0242276 A1    Nov. 3, 2005

(30) Foreign Application Priority Data

Mar. 26, 2004    (JP) ............................. 2004-092915

(51) Int. Cl.
*A61N 5/00* (2006.01)

(52) U.S. Cl. .................................. 250/492.3; 376/190

(58) Field of Classification Search .............. 250/492.3, 250/492.1, 492.21, 505.1, 515.1, 517.1, 363.04; 436/804; 378/143; 315/505; 376/190, 340
See application file for complete search history.

(56) References Cited

U.S. PATENT DOCUMENTS 5,037,602 A    8/1991   Dabiri et al.

FOREIGN PATENT DOCUMENTS

| JP | 04016799 A | * | 1/1992 |
| JP | 4-504174 | | 7/1992 |
| WO | WO90/10937 | | 9/1990 |

* cited by examiner

*Primary Examiner*—Lisa Caputo
*Assistant Examiner*—Michael Maskell
(74) *Attorney, Agent, or Firm*—Crowell & Moring LLP

(57) ABSTRACT

A radioisotope production apparatus includes: a linear accelerator for accelerating an ion beam and irradiating a target with the ion beam, radio frequency power supplies for supplying radio frequency waves through coaxial tubes and the linear accelerator, a target shield member containing the target, a first radiation shield member covering the linear accelerator, and a movable second radiation shield member covering the side of target shield member of the linear accelerator between the first radiation shield member and the target shield member. The first radiation shield member is movably divided in opposite directions, respectively, of the axial direction of the linear accelerator from the base point of the connection point of the coaxial tube connected to the linear accelerator.

13 Claims, 6 Drawing Sheets

RADIOISOTOPE PRODUCTION APPARATUS AND RADIOPHARMACEUTICAL PRODUCTION APPARATUS

FIELD OF THE INVENTION

The present invention relates to a radioisotope production apparatus and a radiopharmaceutical production apparatus, and particularly to a radioisotope production apparatus and a radiopharmaceutical production apparatus, using a linear accelerator, used for the examinations of Positron Emission Tomography (hereinafter, referred to as PET).

BACKGROUND OF THE INVENTION

Recently, the PET examination has attracted attention as an examination method for cancer, encephalopathy, and cardiopathy. In the PET examination, a radiopharmaceutical (referred to as a PET medicine) using nuclides emitting positrons (positive electron) as markers is dosed into the body of a subject, wherein gamma rays emitted outside the body, caused by the PET medicine accumulated at the diseased part or the PET medicine flowing through veins of the brain and the heart, are detected with a plurality of radiation detectors. The information obtained on the basis of the gamma ray detection signals outputted by these radiation detectors is used to provide tomographic images of the subject. Using the tomographic images, diagnosis of the blood flow or the like is carried out.

The PET examination is useful as an examination with a relative low load on patients in addition to the fact that it can find a cancer, for example, having a size equal to or less than 1 cm, which is difficult to be found by examinations with the CT (Computer Tomography, X-ray tomography) apparatus or the MRI (Magnetic Resonance Imaging, nuclear magnetic resonance tomographic imaging) apparatus and the fact that it provides the examination over the whole body of the subject in a shorter interval than that of the conventional examinations.

It is generally known that radioisotopes used in such PET examinations have short half-lives. As the radioisotopes, oxygen 15 ($^{15}O$) having a half-life of about two minutes and fluorine 18 ($^{18}F$) having a half-life of about two hours or the like exist. Particularly, the usefulness of $^{18}F$ rapidly increases because of the relative long half-life as this type of a nuclide.

$^{18}F$ is produced generally by using a nuclear reaction generated by irradiating oxygen 18 ($^{18}O$) with protons having high energy. $^{18}O$ is an isotope of the oxygen 16 ($^{16}O$) and naturally exists only by about 0.2%. Thus, it may be also considered to condense $^{18}O$ to increase the yield. In fact, $^{18}F$ is produced by irradiating a container filled with water containing $^{18}O$ ($H_2{}^{18}O$) with protons accelerated to about 10 MeV. Conventionally, to produce it, the cyclotrons which require relative large facilities are mainly used. Further, a technology for obtaining radioisotopes by irradiation with helium ions by a linear accelerator was also proposed (for example, WO9010937 discloses such a technology at page 9, line 25 to page 17, line 23).

In the general conventional production of $^{18}F$ mentioned above, upon irradiating oxygen 18 ($^{18}O$) with protons having high energy, a nuclear reaction generates rays (neutrons or the like). Thus, in the facilities accommodating the radioisotope production apparatus including an accelerator, it is important to shield against rays. Conventionally, to shield rays, there is a known method, in which thick walls comprising concrete as base members (radiation shield walls) are arranged integrally with the building (a ceiling and a floor) of the facilities around the room in which an accelerator or the like is installed.

However, there is a problem that it takes a long time to arrange thick walls for radiation shielding with much labor, and as well as the building itself should be made strong, so that the cost will increase. Further, there is also a problem that in the existent facility, the location of the radioisotope production apparatus is limited.

Further, as described above, since the half-lives of radioisotopes are relatively short, it is desirable to execute the process from synthesizing of the PET medicine to the PET examination in a short interval, and thus, the medical facilities having such a function have been desired.

SUMMARY OF THE INVENTION

An aspect of the present invention is to provide a radioisotope production apparatus and a radiopharmaceutical production apparatus, superior in a radiation shielding capability and a maintenance capability and capable of reducing cost of building for installation.

Another aspect according to the present invention provides features that the linear accelerator accelerating an ion beam and irradiating a target with the ion beam is covered with a first radiation shield member, the region between the first radiation shield member and a shield for the target is covered with a movable second radiation shield member, and the first radiation shield is movably divided in opposite directions of an axis of the linear accelerator at a base point defined by the radio frequency transmission line connected to the linear accelerator. The first and second radiation shields block rays externally leaked from the linear accelerator, so that the capability of shielding rays can be improved. Further, the first radiation shield member is moveably divided in opposite directions of the axial direction of the linear accelerator at a base point of the radio frequency wave transmission line connected to the linear accelerator. Thus, during non-operation of the linear accelerator, the first radiation shield member is movably divided to provide access to the linear accelerator to improve the maintenance capability of the linear accelerator.

A further aspect according to the present invention provides the second radiation shield member comprises a plurality of second radiation shield sections movable in opposite directions perpendicular to the axis of the linear accelerator. The structure of the second radiation shield member provides the divisional movement of the first radiation shield and the smooth maintenance of the linear accelerator.

Preferably, the second radiation shield member is movable in the axial direction of the linear accelerator either to the outside or the inside of the first radiation shield member.

A further aspect according to the present invention provides a radiopharmaceutical production apparatus comprises a radioisotope production apparatus and a radiopharmaceutical synthesizing apparatus for producing a radiopharmaceutical with the radioisotopes produced within the target, wherein the radioisotope production apparatus is structured such that the linear accelerator accelerating an ion beam and irradiating a target with the ion beam is covered with a first radiation shield member, the region between the first radiation shield member and a shield for the target shield member is covered with a movable second radiation shield member, and the first radiation shield member is movably divided in opposite directions of an axis of the linear accelerator at a base point of the radio frequency transmission line connected to the linear accelerator.

A still further aspect according to the present invention provides a radioisotope production apparatus and a radiopharmaceutical production apparatus with improvement in capability of shielding rays and the maintenance capability.

BRIEF DESCRIPTION OF THE DRAWINGS

The object and features of the present invention will become more readily apparent from the following detailed description taken in conjunction with the accompanying drawings in which.

The same or corresponding elements or parts are designated with like references throughout the drawings.

DETAILED DESCRIPTION OF THE INVENTION

A radiopharmaceutical production apparatus according to a preferred embodiment of the present invention will be described with reference to the accompanied drawings. The radioisotope production apparatus included in the radiopharmaceutical production apparatus according to the embodiment will be mainly described.

Figure 1:
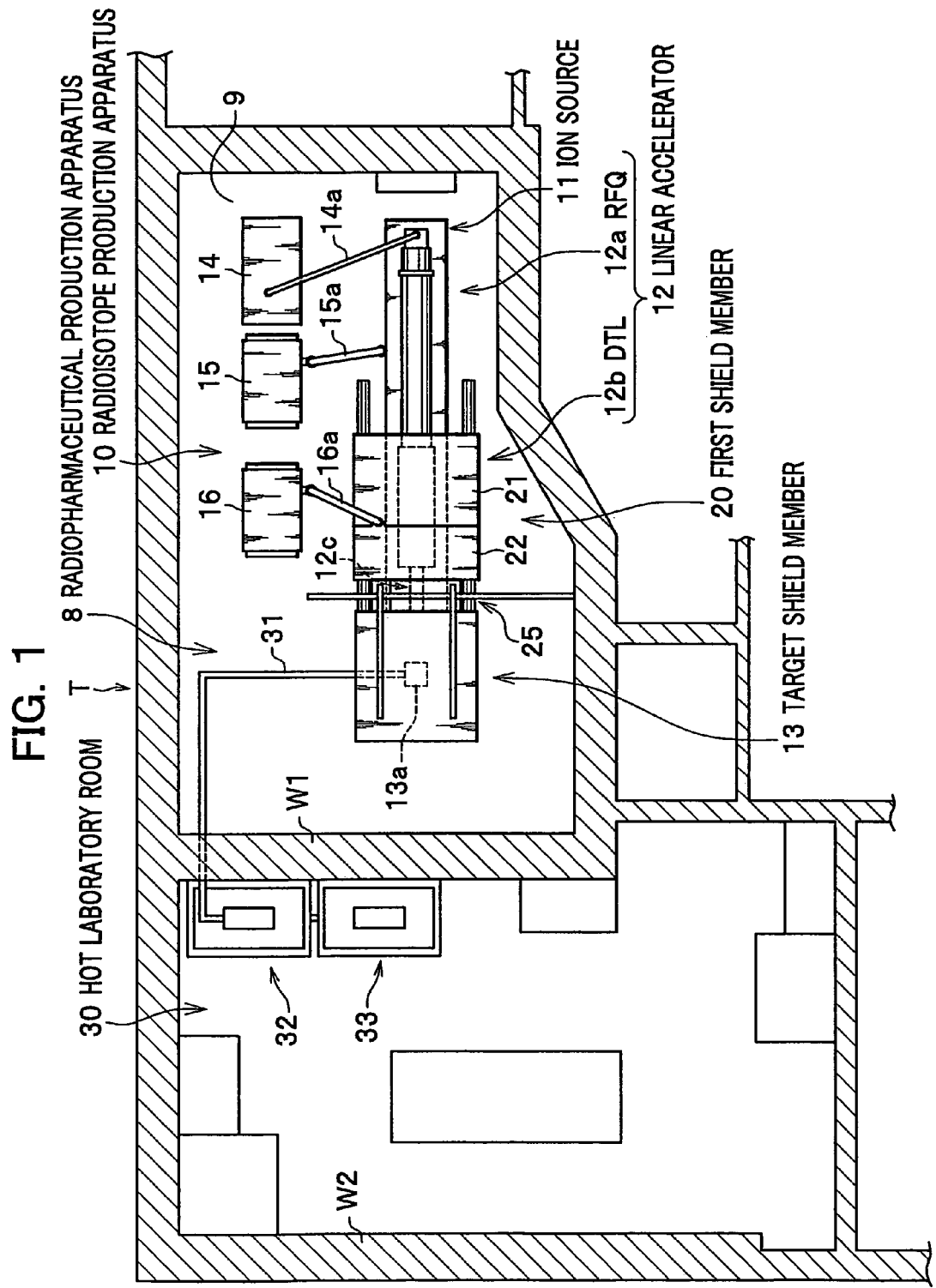
FIG. 1 is a plan view of a radiopharmaceutical production apparatus of an embodiment according to the present invention.
Figure 2:
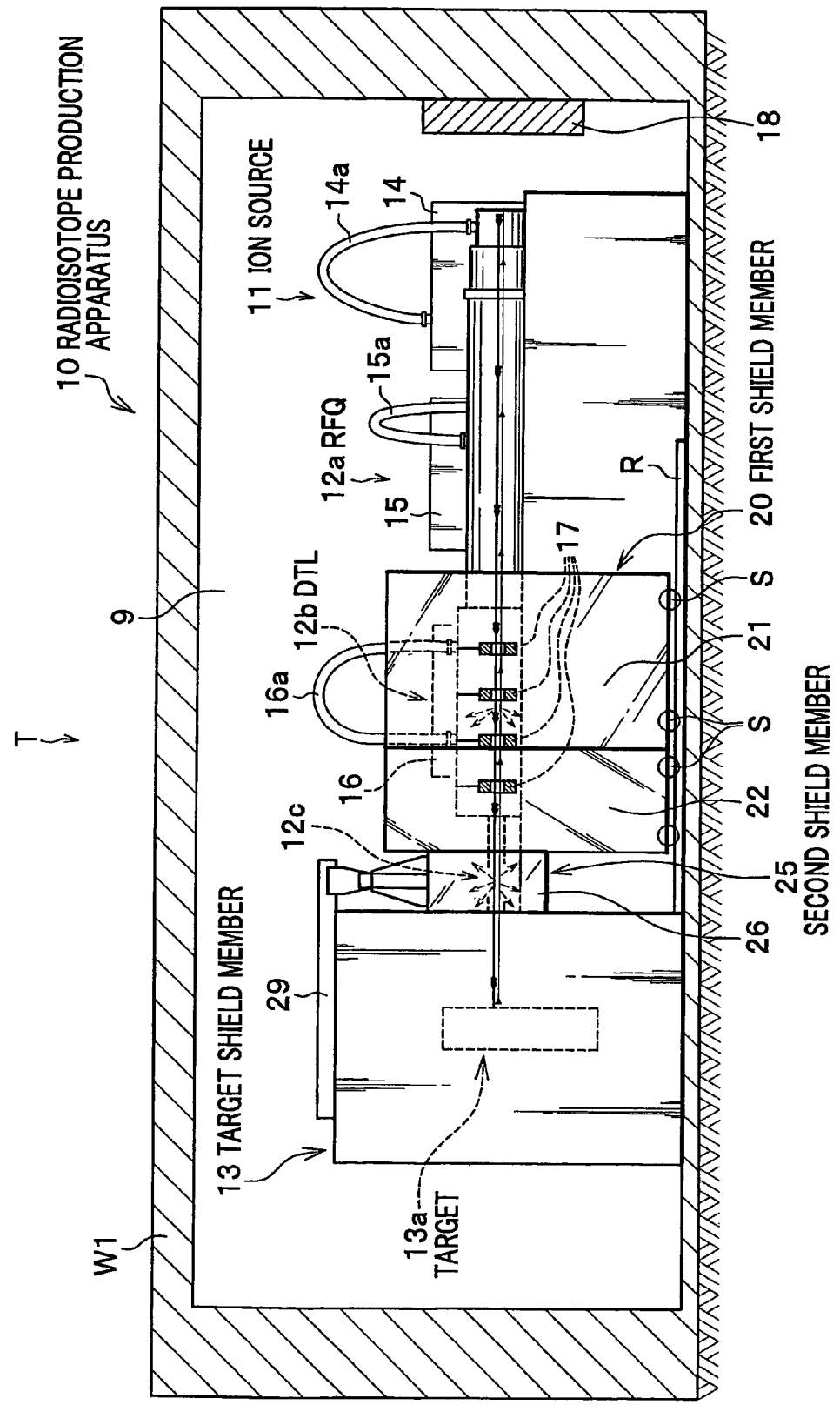
FIG. 2 is a side view of the radioisotope production apparatus shown in FIG. 1.

As shown in FIGS. 1 and 2, a radiopharmaceutical production apparatus 8 according to the embodiment comprises a radioisotope production apparatus 10, a radiopharmaceutical synthesizing apparatus 32, and a medicine dispensing apparatus 33. The radioisotope production apparatus 10 is installed inside an accelerator room 9 in a building T such as a hospital. The radiopharmaceutical synthesizing apparatus 32, and the medicine dispensing apparatus 33 are arranged in a hot laboratory room 30 in the building T. The accelerator room 9 comprises shield walls W1 including base members made of concrete for shielding ray (neutrons or the like) therearound. Further, the hot laboratory room 30 comprises shield walls W2 therearound for mainly shielding gamma rays. In FIG. 1, doors provided to the accelerator room 9 and the hot laboratory room 30 are omitted.

The radioisotope production apparatus 10 comprises an ion source 11, a radio frequency Quadrupole (hereinafter referred to as RFQ) type of a linear accelerator 12a, a drift tube type of linear accelerator (Drift Tube Linac, hereinafter referred to as DTL) 12b and a target 13a. The target 13a is arranged within a target shield member 13. The ion source 11, the RFQ 12a, the DTL 12b are serially arranged within the accelerator room 9 in this order in the traveling direction (the direction from the ion source 11 to the target shield member 13). Further, at the sides of these RFQ 12a and the DTL 12b, radio frequency power supplies 15 and 16 for supplying radio frequency powers to the ion source 11 are arranged and spaced from the RFQ 12a and the DTL 12b, respectively. At the side of the ion source 11, a power supply 14 is arranged and spaced from the ion source 11 to supply electric powers to them. Further, around the DTL 12b, a first radiation shield member (hereinafter, referred to as a first shield member) 20 is provided. Between the DTL 12b and the target shield 13, as shown in FIG. 2, a second radiation shield member (hereinafter a second shield member) 25 is provided.

The ion source 11 operates to ionize the source material to be ionized (here, hydrogen) to produce an ion beam including positive ions. Further, a magnet (not shown) for extracting only desired ions in accordance with the mass, an electric field lens (not shown) for shaping the ion beam, and an ion beam generation section or the like are provided therearound. The ion source 11 is supplied with an electric power through a supply power cable 14a from the power supply 14. In addition, a hot cathode system of duoplasmatron type of ion source or a PIG type of ion source can be used as the ion source 11. Further, the microwave discharge type of ion source having a long life with a large current capacity may be used.

At the rear stage of the ion source 11, the RFQ 12a is arranged, where the ion beam emitted from the ion beam generation section (not shown) is accelerated by the RFQ 12a to have a predetermined energy.

The RFQ 12a comprises a Quadrupole having a wave shape in a vacuum chamber at the inside thereof. Further, at the beam incident section (not shown), a bunching section is formed to bunch ion beam(s) so as to readily accelerate the ion beam. Supplying a radio frequency power having a predetermined frequency to the RFQ 12a from the radio frequency power supply 15 through a coaxial tube 15a produces a Quadrupole electric field in a direction parallel to the traveling direction of the ion beam. This accelerates the ion beam bunched at the beam incident section, wherein the ion beam is converged. The ion beam accelerated by the RFQ 12a is incident to the rear stage of the DTL 12b, which further accelerates the ion beam.

Instead of the RFQ 12a used here, a multi-electrode type of radio frequency accelerator having an even number more than five of magnet poles may be used. Further, other radio frequency accelerators can be used.

The DTL 12b, as shown in FIG. 2, comprises, at the center thereof, a plurality of drift tubes 17 arranged in an axial direction thereof. The drift tube 17 comprises four poles of electromagnets (not shown) built therein, where the ion beam is subjected to convergence during passing therethrough. The acceleration of the ion beam is carried out between these drift tubes 17.

These RFQ 12a and DTL 12b functions, as combination, a linear accelerator 12 finally generating a high energy beam of about 10 MeV. Between the DTL 12b and the target shield member 13, there is provided a coil section 12c supplied with an electric power for controlling the divergence of the ion beam. In addition, under the coil section 12c, instruments or the like (not shown) are arranged.

Furthermore, in order to control the deviation in resonance frequency caused by the expansion and contraction in the container, the electrodes or the like due to heat, the linear accelerator 12 may comprise a tuner (not shown) for adjusting the resonance frequency.

The target shield member 13 comprises side walls and a ceiling each including a concrete base member. The target shield member 13 is fixed to the floor of the accelerator room 9. Within the target shield member 13, a target 13a containing $^{18}O$ is placed. For the method of condensing $^{18}O$ (a refine method), a distillation process, an electrolysis process, a chemical exchange process or the like are adoptive. Further, the laser isotopic enrichment process may be used because it provides a high condense coefficient in a short time interval with a small-sized unit. The target 13a is pressured with an argon gas or the like to prevent boiling. The water containing the generated $^{18}F$ is, as described later, supplied to the hot laboratory room 30 through a tube 31 by the pressurized argon gas.

Figure 3A:
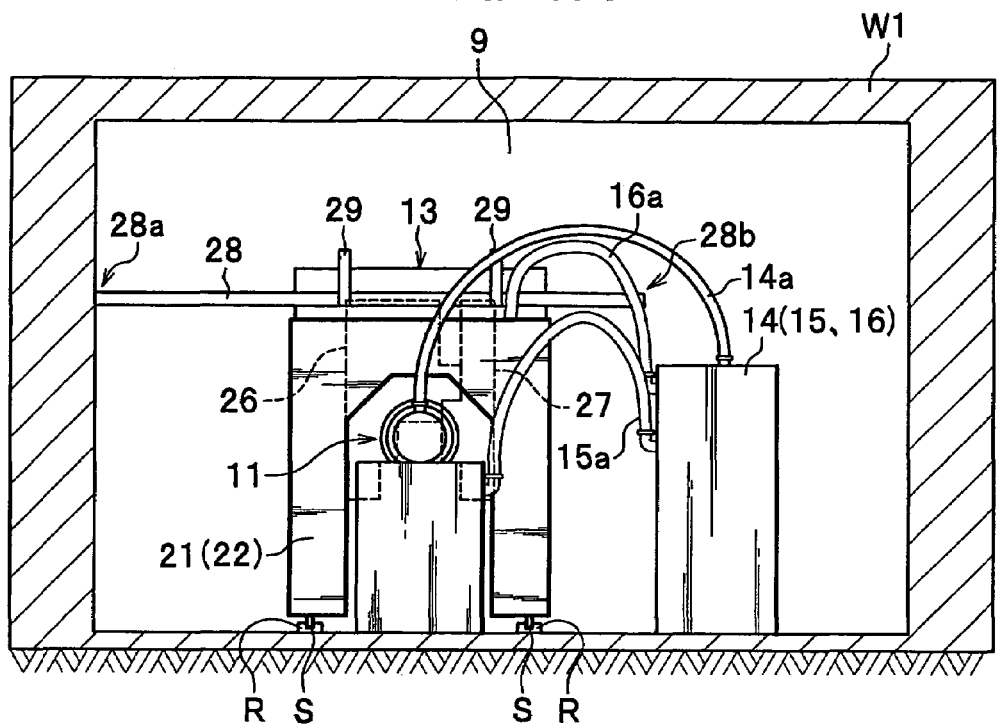
FIG. 3A is a front view illustrating first and second shield members in a closed position according to the present invention.

The ion source 11 is connected to the general power supply 14 through the power cable 14a as described above. The RFQ 12a is connected to the radio frequency power supply 15 with the coaxial tube 15a. The DTL 12b is connected to the radio frequency power supply 16 by the coaxial tube 16a. The power supply 14 and radio frequency power supplies 15 and 16 are arranged at the sides of the ion source 11, the RFQ 12a, and the DTL 12b with spaces therebetween, respectively. Further, the power cable 14a and respective coaxial tubes 15a and 16a, as shown in FIG. 3A, upwardly rise and arranged to have arches thereof so as to form a predetermined passage between the ion source 11, the RFQ 12a, and the DTL 12b and them (the power supply 14 and radio frequency power supplies 15 and 16). The passage can be used as a service space during a maintenance service. Further, instead of the coaxial tubes 15a and 16a, waveguide tubes may be used. The coaxial tube and the waveguide tube are defined as radio frequency transmission lines.

Figure 3B:
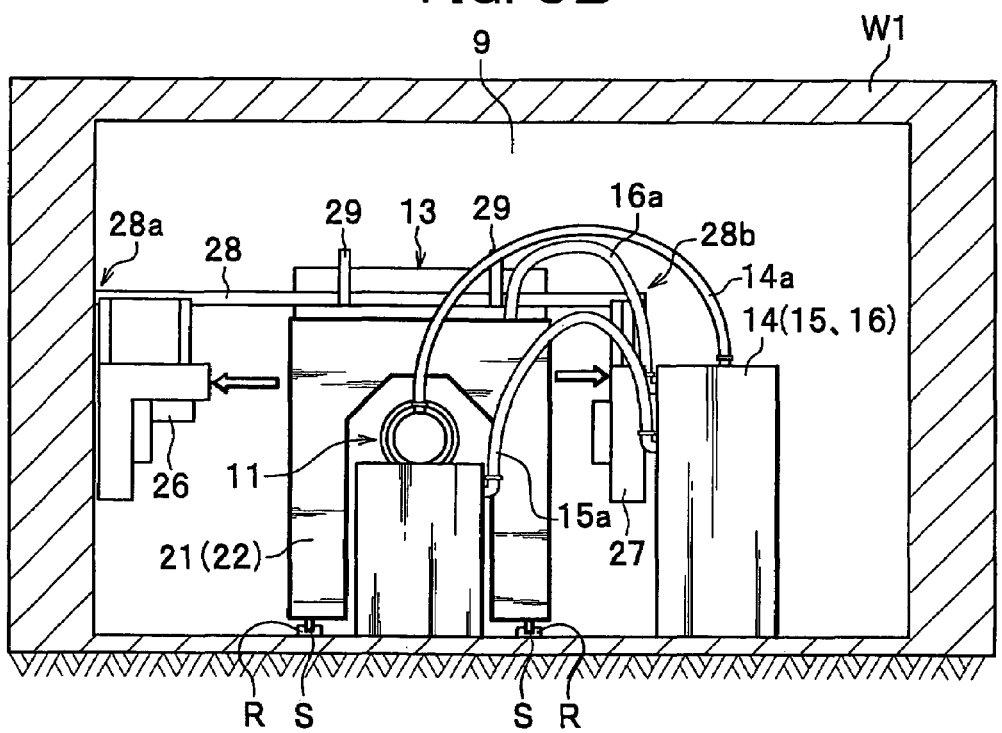
FIG. 3B is a front view illustrating the first and second shield members in an open position according to the present invention.

The first shield member 20 is arranged to cover the DTL 12b and comprises a front radiation shield section (hereinafter referred to as a front section) 21 and a rear radiation shield section (hereinafter referred to as a rear section) 22 as divided members of the first shield member 20. The front section 21 and the rear section 22 each comprises one pair of side wall sections confronting each other and a ceiling section connecting these side wall sections (refer to FIGS. 3A and 3B). The DTL 12b is arranged between pairs of side wall sections of the front section 21 and the rear section 22. At the lower end sections of pairs of side wall sections, a plurality of wheels S are provided (see FIG. 2). These wheels S are placed on a pair of rails (guide members) R arranged on the floor of the accelerator room 9 (refer to FIGS. 3A and 3B). The front section 21 and the rear section 22 are movable in the axial direction of the DTL 12b on the rails R. More specifically, the rear section 22 is movable toward the target shield member 13 from the base point of the vertical section of the coaxial tube 16a upwardly extending from the connection 12d (FIG. 4B) of the DTL 12b. The front section 21 is movable in the opposite direction of the movement of the rear section 22, that is, movable from the vertical section of the coaxial tube 16a as the base point toward the side of the RFQ 12a.

The first shield member 20 has such a divisional structure that the first shield member 20 is divided along a line perpendicular to the axial direction of the DTL 12b including the base point of the vertical section of the coaxial tube 16a and the divided members are movable in opposite directions of the axial direction of the DTL 12b as mentioned above. This provides a shielding (radioactive shielding) condition to shield rays from the DTL 12b in operation of the linear accelerator 12, wherein the front section 21 is in contact with the rear section 22 (see FIG. 4A) and an open condition upon the maintenance service for the DTL 12b, wherein the front section 21 and the rear section 22 are spaced (see FIG. 4B). At the contact surfaces of the front section 21 and the rear section 22 therebetween, a notch section 21a and a protrusion section 22a are formed to provide an insertion hole for the coaxial tube 16a. Upon shielding the rays, the coaxial tube 16a is pinched between the front section 21 and the rear section 22, i.e., the notch section 21a and the protrusion section 22a. In other words, the first shield member 20 includes two first radiation shield sections (the front section 21 and the rear section 22) movable in opposite direction of the axial direction of the DTL 12b.

The first shield member 20, i.e., each of the front section 21 and the rear section 22, is formed, for example, by laminating a plurality of plates molded with polyethylene including boron to have a sufficient thickness.

Figure 4A:
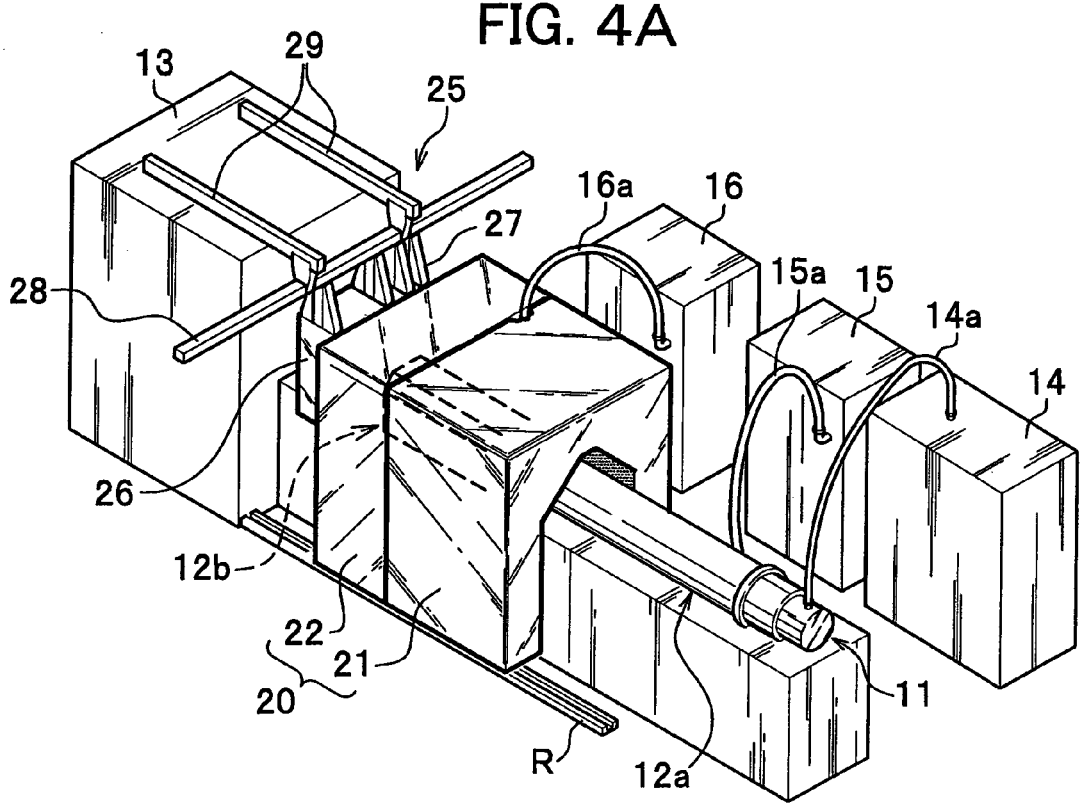
FIG. 4A is a perspective view illustrating the first and second shield members in the closed position according to the present invention.
Figure 4B:
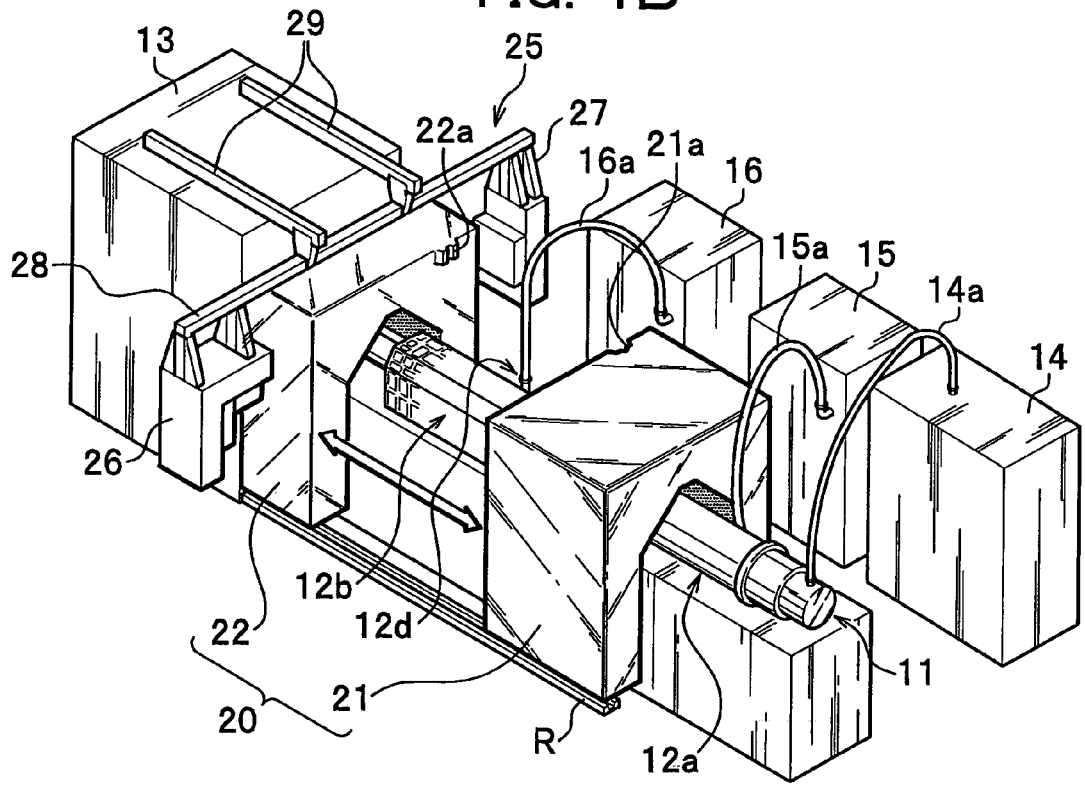
FIG. 4B is a perspective view illustrating the first and second shield members in the open position according to the present invention.

As shown in FIG. 2, the second shield member 25 is arranged between the first shield member 20 (the rear section 22) and the target shield member 13 and comprises a pair of side wall sections and a ceiling section to cover the coil section 12c arranged on the side of the rear stage of the DTL 12b. In this embodiment, as shown in FIG. 4B, when the rear section 22 of the first shield member 20 is moved toward the target shield member 13, the second shield member 25 is movable to positions where interference with the moved rear section 22 is prevented, i.e., movable in a direction perpendicular to the axis of the DTL 12b. To provide this structure, the second shield member 25 comprises a left radiation shield section (hereinafter referred to as a left section) 26 having an inverse-L shape and a right radiation shield section (hereinafter referred to as a right section) 27 having a fitting surface for fitting it into the left section 26. The left section 26 comprises one side wall section and a ceiling section arranged at the upper end of the side wall section. The right section 27 comprises a side wall section confronting the side wall section of the left section 26. A guide rail 28 for guiding these left section 26 and right section 27 in the left and right directions (the direction perpendicular to the axis of the DTL 12b), respectively, is supported by a pair of stays 29 fixed to the upper surface of the target shield member 13. Furthermore, the left section 26 and the right section 27 are also moved upon a maintenance service for the coil section 12c (see FIG. 2), to the left and the right along the rail (guide member) 28. In other words, the second shield member 25 includes two second radiation shield sections (the left section 26 and the right section 27) movable in opposite directions of the direction perpendicular to the axis of the DTL 12b (the direction intersecting with the axis of the DTL 12b), respectively.

The left section 26 and the right section 27 are formed, like the first shield member 20, for example, by laminating a plurality of plates molded with polyethylene including boron to have the desired shape. The second shield member 25 is formed such that, as described above, a pair of the side wall sections thereof face each other and the ceiling section of the left section 26 is in contact with the side wall of the right section 27 in the condition that the left section 26 is fit into the right section 27. The second shield member 25 is opened at the lower part thereof to decrease its weight. Further, the second shield member 25 may comprise, at the lower part of the side wall section of the left section 26, a horizontal section formed to be positioned under the coil section 12c.

The rail 28 has strength enough to withstand the weights of the left section 26 and the right section 27 and is, as shown in FIG. 3A, fixed to the wall W1 at its one end 28a in addition to the support by the stays 29. Further, the other end 28b of the rail 28 is supported by a supporting member (not shown) vertically arranged at the floor. Further, the end 28b may be fixed to the adjacent wall W1.

Next, will be described an operation of the radioisotope production apparatus 10 constructed as mentioned above. In operation of the radioisotope production apparatus 10, the first shield member 20 and the second shield member 25 are previously set in the closed conditions, respectively. That is, the DTL 12b is, as shown in FIG. 4A, covered with the first shield member 20 in which the front section 21 and the rear section 22 are in contact with each other. Further, the coil section 12c (see FIG. 2) is, as shown in FIGS. 3A and 4A, covered with the second shield member 2, wherein the left section 26 is in contact with the right section 27. In addition, the target 13a is previously contained within the target shield member 13.

A predetermined electric power is supplied from the power supply 14 to the ion source 11 through the power cable 14a. After this, operating an operation switch (not shown) supplies predetermined radio frequency electric powers from the radio frequency power supplies 15 and 16 to the RFQ 12a and the DTL 12b to form electrostatic fields at the RFQ 12a and the DTL 12a, respectively. Thus, the RFQ 12a accelerates the ion beam (proton ray) emitted by the ion beam generation section (not shown) of the ion source 11 to have a predetermined energy. The accelerated ion bean is emitted by the RFQ 12a to the rear stage of the DTL 12b, where the ion beam is further accelerated.

The ion beam accelerated by the DTL 12b travels through the coil section 12c and hits the $^{18}$O-enriched water within the target 13a. The irradiation of the ion beams on the $^{18}$O generates $^{18}$F.

The reaction of generation of $^{18}$F produces neutrons which equi-angularly scatter therefrom. At this point, a phenomenon occurs in which a part of the neutrons return from the inside of the target shield member 13 through the ion beam path (backwardly travels through the ion beam path), via the coil section 12c, the DTL 12b, and the RFQ 12 to the ion source 11. In this process, as shown in FIG. 2, a phenomenon occurs in which mainly at the coil section 12c and the DTL 12b near the target shield member 13, neutrons advancing slantwise through the ion beam incident path change the direction and thus splash in all directions. That is, the neutrons collide with coils or the like provided at the coil section 12c and thus, scatter in various directions. In the DTL 12b, the slantwise advancing neutrons collide with members having a certain density, for example, the drift tubes 17 and scatter in various directions.

Though such a phenomenon occurs, the DTL 12b is covered with the first shield member 20, and the coil section 12c is covered with the second shield member 25, so that the neutrons outwardly scattering therefrom are preferably attenuated by the first shielded member 20 and the second shield member 25 and thus, are shielded. Further, gamma rays emitted in the process in which the neutrons are attenuated are also preferably attenuated by the first shield member 20 and the second shield member 25 and thus shielding is provided.

This largely decreases the amount of the neutrons emitted to the accelerator room 9 from the radioisotope production apparatus 10. Further, the neutrons straightly travels backwardly through the ion beam path and returns therefrom are attenuated and shielded by a radiation shield plate 18 arranged on the line extended from the axis of the linear accelerator 12.

As mentioned above, the first shield member 20 and the second shield member 25 cover the DTL 12b and the coil section 12c to preferably attenuate the neutrons to shield the neutrons. Upon the maintenance service of the coil section 12c and the DTL 12b or the like in the case of a stop of the radioisotope production apparatus 10, dividing and moving the first and second shield member 20 and 25 makes the coil section 12c and the DTL 12b in the exposed condition. Here, the first shield member 20 and the second shield member 25 are moved as follows:

As shown in FIG. 4B, first, fitting between the left section 26 and the right section 27 of the second shield member 25 is released to move the left section 26 and the right section 27 individually to the left and the right, respectively at the position of the coil section 12c. Next, the front section 21 and the rear section 22 of the first shield member 20 are individually moved backward and forward as described above. This makes the DTL 12b in the exposed condition. At this point, the movement of the rear section 22 to the target shield member 13 is permitted by previously moving the left section 26 and the right section 27 of the second shield member 25 to expose the part of the coil section 12c. This allows the rear section 22 to be moved to the position of the coil section 12c. Thus the maintenance service of the exposed DTL 12b is made easy. Upon the maintenance of the coil section 12c, the rear section 22 is moved to the position of the vertical section of the coaxial tube 16a to expose the coil section 12c. The maintenance service of the coil section 12c is also possible to be executed before the movement of the rear section 22 to the side of the target shield member 13. Thus, the arrangement of the first shield member 20 and the second shield member 25 efficiently attenuate the neutrons or the like emitted from the coil section 12c and the DTL 12b to shield the neutrons and provides an advantageous effect that the maintenance of the coil section 12c and the DTL 12b is readily carried out.

Next, will be described the process for producing the PET medicine using the $^{18}$O-enriched water containing $^{18}$F in the target 13a with reference to FIG. 1 again.

The tube 31 is connected to the target 13a. The produced water containing $^{18}$F is supplied to the radioisotope medicine synthesizing apparatus 32 in the hot laboratory room 30 through the tube 31 by pressurizing the target 13a with argon gas or the like having a high pressure. The wall W1 between the accelerator room 9 and the hot laboratory room 30 comprises concrete as a base member that can attenuate rays (neutrons or the like).

At the hot laboratory room 30, there are the radiopharmaceutical synthesizing apparatus 32 for synthesizing the PET medicine from the water containing $^{18}$F supplied through the tube 31 and the medicine dispensing apparatus 33 for dispensing the PET medicine. Further, at the hot laboratory room 30, an intake blower (not shown) and the well-known HEPA filter (not shown) or the like are provided to feed the air through the HEPA filter to the inside of the hot laboratory room 30.

The radiopharmaceutical synthesizing apparatus 32 synthesizes the PET medicine on the basis of the water containing $^{18}$F. More specifically, the radiopharmaceutical synthesizing apparatus 32 extracts $^{18}$F from the condensed water containing $^{18}$F to synthesize FDG (fluorodeoxyglucose). The PET medicine is produced as mentioned above.

The medicine dispensing apparatus 33 automatically dispenses the synthesized PET medicine to have a desired amount of the PET medicine for each subject in accordance with the weight or the like of the subject. The dispensed PET medicine is put into a container. The medicine dispensing apparatus 33 automatically executes this dispensing operation. Since the remaining condensed water of $^{18}$O from which the $^{18}$F is extracted is very expensive, it is desirable to reuse the remaining condensed water in the target 13a after collecting it.

In the above-described radioisotope production apparatus 10 according to the present embodiment, the DTL 12b accelerating an ion beam to irradiate the target 13a with the ion beam is covered with the first shield member 20, as well as the coil section 12c positioned on the side of the target shield member 13 with respect to the linear accelerator 12 (DTL 12b) is covered with the second shield member 25 between the first shield member 20 and the target shield member 13. This structure provides shielding by attenuating the neutrons emitted from the DTL 12b and the coil section 12c by these shield members to largely reduce the amount of the neutrons externally leaking therefrom.

This eliminates the necessity of forming thick shielding walls in the building that were conventionally necessary, and thus, also eliminates the necessity of strengthening the structure of the building. This provides an advantageous effect of the shortened construction period of the building.

Further, this also provides an advantageous effect that the radioisotope production apparatus 10 can be installed even at a location that cannot support the conventional thick walls due to, for example, its structure.

Further, since the first shield member 20 and the second shield member 25 are movably provided, the maintenance service for the linear accelerator 12 (DTL 12b) and the coil section 12c can be easily carried out. That is, this improves the maintenance capability of the linear accelerator 12 (DTL 12b) and the coil section 12c.

More specifically, the first shield member 20 is movably divided at the vertical section of the coaxial tube 16a connected to the linear accelerator 12 (DTL 12b) as the base point in the axial direction of the DTL 12b, so that upon non-operation, the DTL 12b can be exposed by movably dividing the first shield member 20 into the front section 25 and the rear section 22. Therefore, there is provided the radioisotope production apparatus with the shield structure in which neutrons or the like are attenuated as well as with the convenience structure in carrying out maintenance services.

Further, the second shield member 25 can be movably divided to the left and the right (into the-left section 26 and the right section 27), so that the rear section 22 of the first shield member 20 can be moved toward the side of the target shield member 13 to expose the DTL 12b. This provides a preferable maintenance for the DTL 12b.

It is important that the first shield member 20 is divided at the base point of the coaxial tube 16a. More specifically, the first shield member 20 is made up of the rear section 22 movable from the coaxial tube 16a toward the side of the target shield member 13 and the front section 21 movable from the coaxial tube 16a toward the side of the RFQ 12a. This allows the rear section 22 and the front section 21 to move in the axial direction of the linear accelerator 12. This provides the radiation shield by covering the DTL 12b with the rear section 22 and the front section 21 and the exposure of the DTL 12b for the maintenance service by the movement of the rear section 22 and the front section 21 in the above-mentioned directions, respectively. Here, if it is assumed that the rear section 22 and the front section 21 are combined to form the first shield member, the coaxial tube 16a should pierce through the first shield member. This prevents the first shield member 20 from moving in the axial direction of the linear accelerator 12 because of the existence of the fixed coaxial tube 16a. Thus, the exposure of the DTL 12b for the maintenance service would be impossible. On the other hand, according to the present embodiment, the rear section 22 and the front section 21 are movable from the base point of the coaxial tube 16a as mentioned above. This provides both the radiation shielding and the maintenance capability.

The left section 26 and the right section 27 of the second shield member 25 are movable along the rail 28 arranged above the second shield member 25, so that instruments or the like can be arranged on the side of the coil section 12c. In other words, though the instruments or the like are arranged on the side of the coil section 12c, the left section 26 and the right section 27 are movable by the rail 28. This provides the exposure of the coil section 12c.

The radioisotope production apparatus 10 can supply the condensed water containing $^{18}$F produced thereby through the tube 31 to the hot laboratory room 30 adjacently provided to synthesize the PET medicine with the radiopharmaceutical synthesizing apparatus 32 and to dispense it with the medicine dispensing apparatus 33. Thus, the process from the production of the $^{18}$F to the synthesizing the PET medicine can be achieved within the one building to make the interval up to dosing it after synthesizing the PET medicine as short as possible. This provides the efficient use of the PET medicine. More specifically, this also provides an advantageous effect in that the decrease amount of the $^{18}$F medicine after the production thereof up to the use can be considerably suppressed.

Further, the $^{18}$F medicine was conventionally produced to have a rather greater amount thereof. However, the amount of $^{18}$F in the medicine can be reduced in this embodiment.

Figure 5:
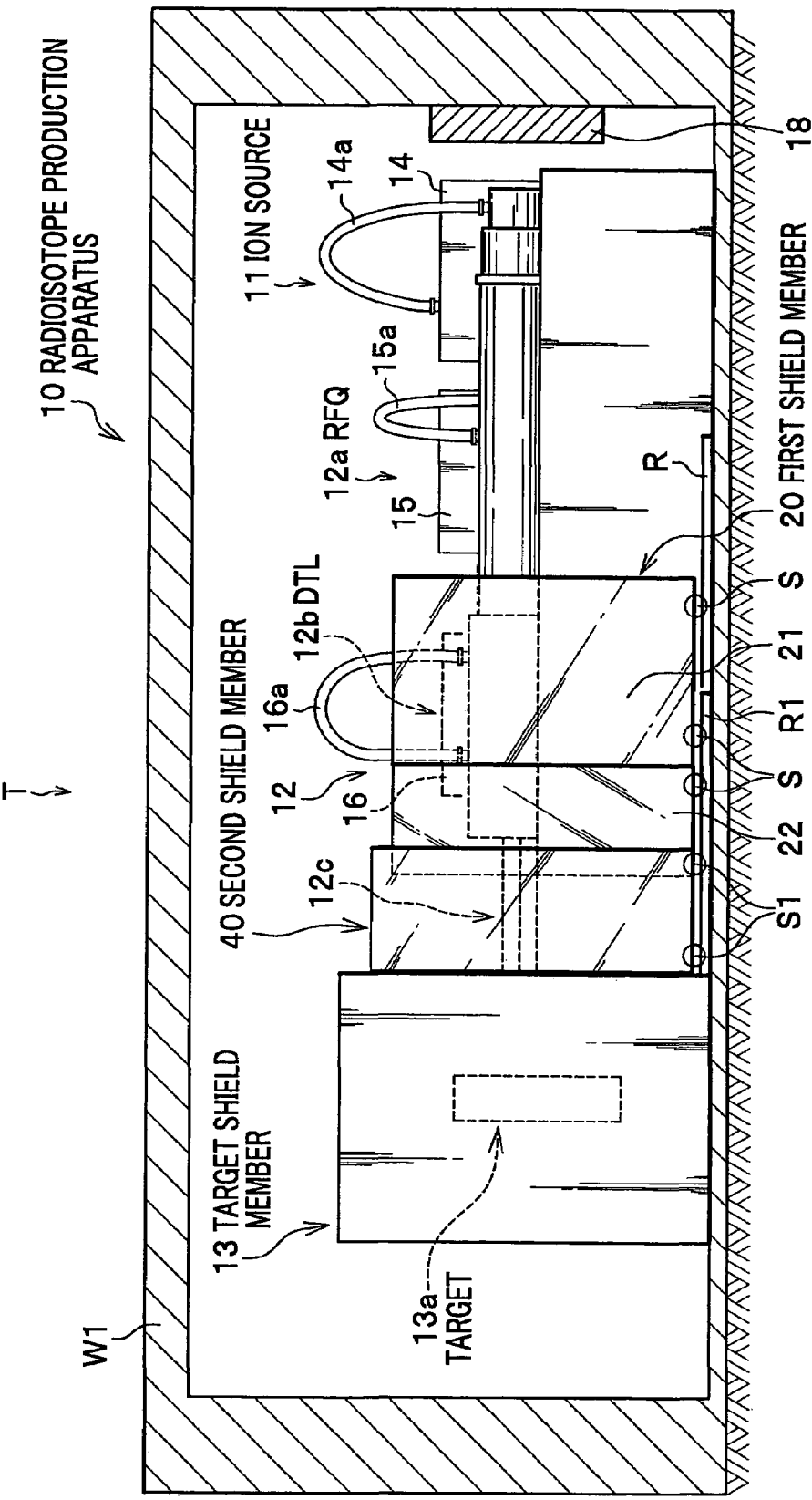
FIG. 5 is a side view of another embodiment of the radioisotope production apparatus according to the present invention.
Figure 6A:
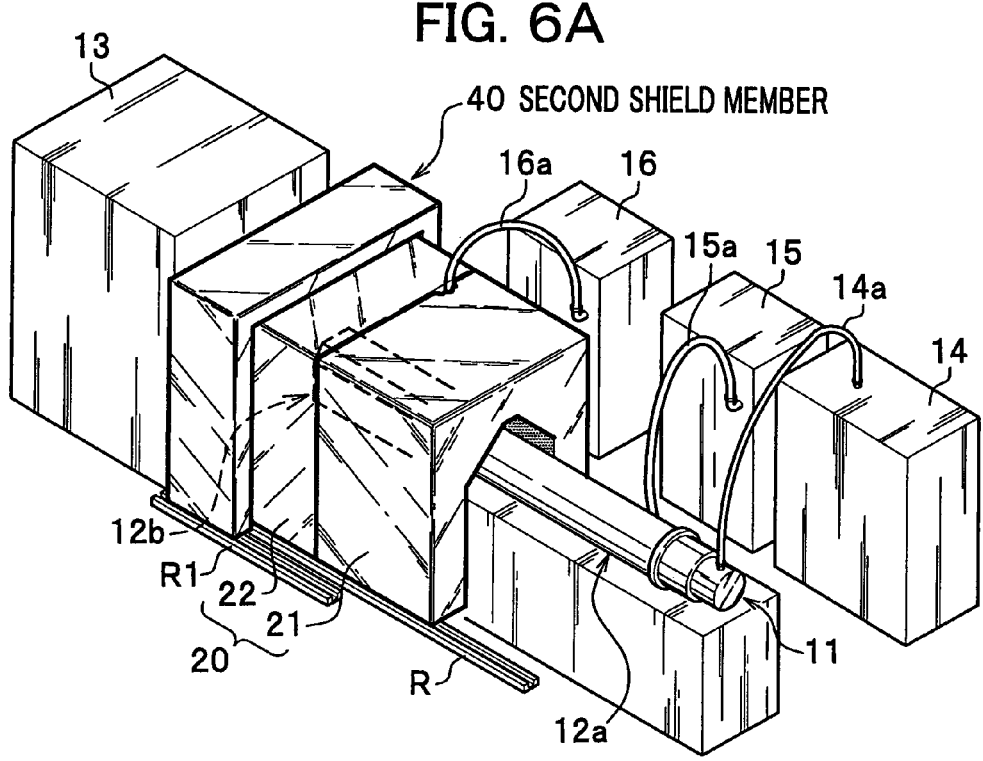
FIG. 6A is a perspective view illustrating the first and second shield members shown in FIG. 5 in a closed position.
Figure 6B:
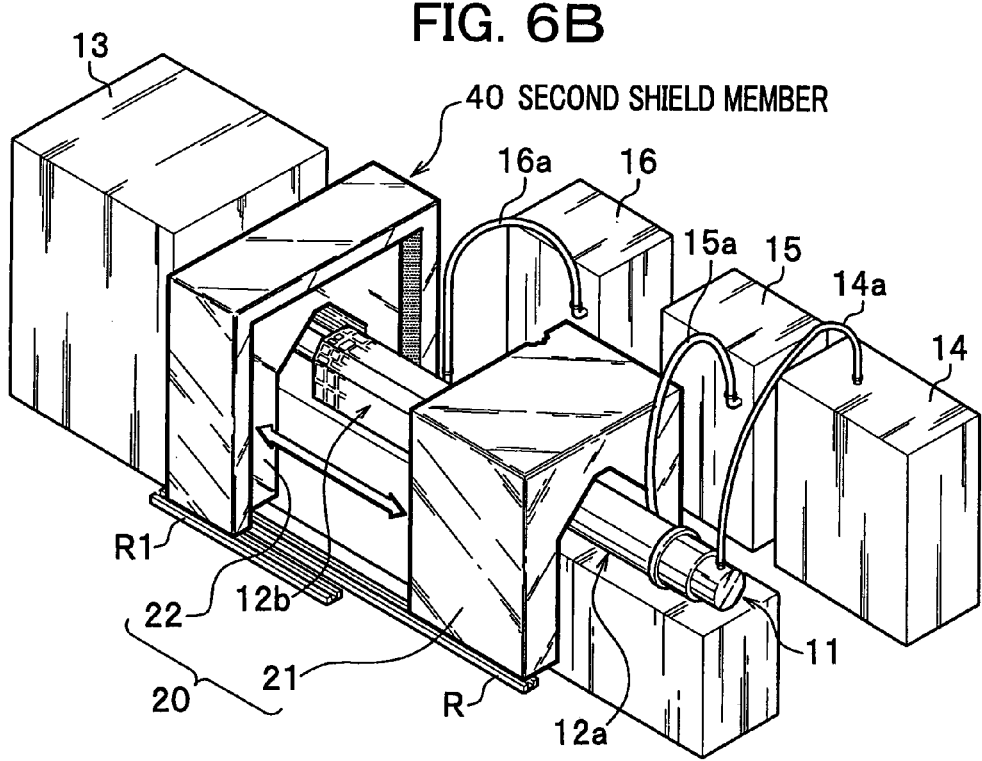
FIG. 6B is a perspective view illustrating these first and second shield members in an open position according to the present invention.

As the embodiment of the present invention has been described above, this invention should not be limited to the above described embodiment and modifications may be made without departing from sprits of the subject of the present invention. For example, as shown in FIGS. 5 and 6A and 6B, the second shield member 40 may be, like the first shield member 20, made up of a pair of confronting side wall sections and a ceiling connecting the upper ends of these side wall sections. The length between the inner surfaces of the side wall sections of the second shield member 40 confronting each other is larger than that of the outer surfaces of the side wall sections of the first shield member 20 confronting each other. The position of the lower surface of the ceiling section of the second shield member 40 is higher than the position of the upper surface of the ceiling of the first shield member 20. A plurality of wheels are provided to the lower end section of each of a pair of side wall sections of the second shield member 40. Thus, placing the wheels S1 on a pair of the rails (guide members) R1 arranged on the floor of the accelerator room 9 allows the movement of the second shield member 40 in the axial direction of the linear accelerator 12. These rails R1 are positioned outside the rails R, so that the second shield member 40 bridges the first shield member 20 and thus, is movable in its axial direction.

When the rear section 22 of the first shield member 20 is moved toward the target shield member 13, it enters the inside of the second shield member 40. Thus, the first shield member 20 is placed either in the condition that the DTL 12b is covered as shown in FIG. 6A or in the condition that the front section 21 and the rear section 22 are apart from each other to expose the DTL 12b as shown in FIG. 6B. Further, the movement of the second shield member 40 toward the side of the first shield member 20 (the rear section 22) provides the exposure of the coil section 12c. Contrarily, when the second shield member 40 is in contact with the target shield member 13, the coil section 12c is covered with the second shield member 40. The installation of the first shield member 20 and the second shield member 40 as described above can also shield neutrons emitted by the DTL 12b and the coil section 12c like the first shield member 20 and the second shield member 25 are installed. This makes the maintenance service for the exposed DTL 12b and coil section 12c easy.

Further, the second shield member 40 may be moved into the inside of the first shield member 20 by the making the second shield member 40 smaller than the first shield member 20. Further, in the above-mentioned respective embodiments, the first shield member 20 covers the DTL 12b. However, the present invention is not limited to this, but the first shield member 20 may cover the RFQ 12a or both the DTL 12b and the RFQ 12a or cover a part of them.

The invention claimed is:

1. A radioisotope production apparatus comprising:
an ion source for emitting an ion beam;
a linear accelerator for accelerating said ion beam emitted from said ion source and irradiating a target with said accelerated ion beam;
a radio frequency power supply for supplying a radio frequency wave to said linear accelerator through a radio frequency wave transmission line;
a target shield member for accommodating and shielding said target;
a first radiation shield member for covering and shielding said linear accelerator; and
a movable second radiation shield member for covering and shielding a region between said first radiation shield member and said target shield member, wherein said first radiation shield member is divided at a base point defined by said radio frequency wave transmission line connected to said linear accelerator, and the divided members are movable in opposite directions, respectively, of an axis of said linear accelerator.

2. The radioisotope production apparatus as claimed in claim 1, wherein said second radiation shield member is arranged between said linear accelerator and said target shield member and covers a coil section arranged between said linear accelerator and said target for controlling divergence of said ion beam injected by said linear accelerator to irradiate said target with said ion beams.

3. The radioisotope production apparatus as claimed in claim 1, wherein said second radiation shield member is movably divided in opposite directions perpendicular to the axis of said linear accelerator.

4. A radioisotope production apparatus comprising:
an ion source for emitting an ion beam;
a linear accelerator for accelerating said ion beam emitted from said ion source and irradiating a target with said accelerated ion beam;
a radio frequency power supply for supplying a radio frequency wave to said linear accelerator through a radio frequency wave transmission line;
a target shield member for accommodating and shielding said target;
a first radiation shield member for covering and shielding said linear accelerator; and
a movable second radiation shield member for covering and shielding a region between said first radiation shield member and said target shield member, wherein said first radiation shield member comprises a plurality of first shielding sections that are movable from a base point defined by said radio frequency wave transmission line connected to said linear accelerator in opposite directions of an axis of said linear accelerator.

5. The radioisotope production apparatus as claimed in claim 4, wherein said second radiation shield member is arranged between said linear accelerator and said target shield member and covers a coil section arranged between said linear accelerator and said target for controlling divergence of said ion beam injected by said linear accelerator to irradiate said target with said ion beams.

6. The radioisotope production apparatus as claimed in claim 4, wherein said second radiation shield member is movably divided in opposite directions perpendicular to the axis of said linear accelerator.

7. The radioisotope production apparatus as claimed in claim 4, wherein said second radiation shield member comprises a plurality of second radiation shield sections movable in opposite directions, respectively, perpendicular to the axis of said linear accelerator.

8. The radioisotope production apparatus as claimed in claim 7, wherein said second radiation shield sections are movable on a guide member arranged above said linear accelerator.

9. The radioisotope production apparatus as claimed in claim 8, wherein said guide member is supported by said target shield member.

10. The radioisotope production apparatus as claimed in claim 4, wherein a plurality of said first radiation shield members are movable on guide members arranged on a floor surface on which said linear accelerator is arranged.

11. A radioisotope production apparatus comprising:
an ion source for emitting an ion beam;
a linear accelerator for accelerating said ion beam emitted from said ion source and irradiating a target with said accelerated ion beam;
a radio frequency power supply for supplying a radio frequency wave to said linear accelerator through a radio frequency wave transmission line;
a target shield member for accommodating and shielding said target;
a first radiation shield member for covering and shielding said linear accelerator; and
a movable second radiation shield member for covering and shielding a region between said first radiation shield member and said target shield member, wherein said first radiation shield member comprises a plurality of first shielding sections that are movable from a base point defined by said radio frequency wave transmission line connected to said linear accelerator in opposite directions, respectively, of an axis of said linear accelerator, and said second radiation shield member is movable in an axial direction of said linear accelerator either of inside or outside said first radiation shield member when said first radiation shield member and said second radiation shield member overlap with each other.

12. The radioisotope production apparatus as claimed in claim 11, wherein said first radiation shield member is movable on first guide members arranged on a floor surface on which said linear accelerator is arranged, and said second radiation shield member is movable on second guide members arranged on said floor surface in parallel to said first guide members.

13. A radiopharmaceutical production apparatus comprising:
a radioisotope production apparatus comprising:
an ion source for emitting an ion beam;
a linear accelerator for accelerating said ion beam emitted from said ion source and irradiating a target with said accelerated ion beam to produce radioisotope in said target;
a radio frequency power supply for supplying a radio frequency wave to said linear accelerator through a radio frequency wave transmission line;
a target shield member for accommodating and shielding said target;

a first radiation shield member for covering and shielding said linear accelerator; and a movable second radiation shield member for covering and shielding a region between said first radiation shield member and said target shield member, wherein said first radiation shield member is divided at a base point defined by said radio frequency wave transmission line connected to said linear accelerator, and the divided members are movable in opposite directions, respectively, of an axis of said linear accelerator; and radiopharmaceutical synthesizing apparatus for producing a radiopharmaceutical using said radioisotope produced by said radioisotope production apparatus.

* * * * *